United States Patent [19]

Vigneaux

[11] Patent Number: 4,974,446
[45] Date of Patent: Dec. 4, 1990

[54] METHOD AND APPARATUS FOR ANALYZING A MULTI-PHASE FLOW IN A HYDROCARBON WELL

[75] Inventor: Pierre Vigneaux, Moisenay, France

[73] Assignee: Schlumberger Technology Corporation, New York, N.Y.

[21] Appl. No.: 413,426

[22] Filed: Sep. 27, 1989

[30] Foreign Application Priority Data

Sep. 29, 1988 [FR] France ................ 88 12729

[51] Int. Cl.$^5$ ............................................. E21B 47/00
[52] U.S. Cl. ............................ 73/155; 73/861.04
[58] Field of Search ............. 73/61.1 R, 155, 861.04; 324/351; 166/250, 264

[56] References Cited

U.S. PATENT DOCUMENTS

| | | | |
|---|---|---|---|
| 3,455,157 | 7/1969 | Lahaye et al. | 73/151 |
| 3,630,078 | 12/1971 | Bonnet | 73/155 |
| 3,721,121 | 3/1973 | Fierfort | 73/155 |
| 3,792,347 | 2/1974 | Hawley | 324/30 |
| 3,909,603 | 9/1975 | Nicolas | 235/151 |
| 4,435,978 | 3/1984 | Glatz | 73/155 |
| 4,441,362 | 4/1984 | Carlson | 73/155 |
| 4,442,711 | 4/1984 | Hulin et al. | 73/155 |

FOREIGN PATENT DOCUMENTS

| | | |
|---|---|---|
| 2558588 | 7/1977 | Fed. Rep. of Germany . |
| 2110377 | 6/1983 | United Kingdom . |
| 2118723 | 11/1983 | United Kingdom . |
| 2123062 | 1/1984 | United Kingdom . |

OTHER PUBLICATIONS

F. Danel, Mesure Locale dans les Ecoulements Diphasiques: Developpements Recents des Sondes Optiques; La Houille Blanche-No. 5–1978; pp. 351–355.

Primary Examiner—Hezron E. Williams
Assistant Examiner—Kevin D. O'Shea
Attorney, Agent, or Firm—Clifford L. Tager

[57] ABSTRACT

This invention relates to methods and apparatus for analyzing a multi-phase fluid flowing along a hydrocarbon well in order to determine, at each depth, the average static proportion of one of the phases by means of a local measurement. At each depth the local static proportion of the phase under investigation is determined at a point in the flow, which point is situated on a circle having a radius r in the transverse-section corresponding to the depth, where the radius r is substantially equal to 0.7 R, and R is equal to radius of the well. The local static proportion at this point is related to the average static proportion by a determined relationship.

24 Claims, 7 Drawing Sheets

FIG_3

FIG_5

FIG_6

FIG_4

FIG_7

FIG_8

FIG_16

FIG_15

METHOD AND APPARATUS FOR ANALYZING A MULTI-PHASE FLOW IN A HYDROCARBON WELL

BACKGROUND OF THE INVENTION

1. Field of the Invention

The present invention relates to a well logging method and apparatus for determining a parameter characteristic of a multi-phase mixture of fluids flowing in a hydrocarbon well during production, e.g. two-phase water-oil mixture or a three-phase water-oil-gas mixture.

2. Description of Prior Art

After evaluating the production capacity of a hydrocarbon well, the well previously cased and cemented is perforated at various depths in order to allow production fluid to rise to the surface. The fluid recovered at the surface may, in fact, comprise a mixture of oil, water, and gas. One of the aims of production logging measurements is to establish not only the nature but also the respective quantitative magnitudes of these phases at each depth.

It is thus important to establish the proportion of the flow attributable to each phase, which proportion is known as the "dynamic" portion or "cut", and comprises the flowrate of each phase divided by the total flowrate. In an oil well, the water and oil phases move at different speeds, with the lighter phase flowing faster than the heavier phase. In addition, the velocity at which one phase slips relative to the other increases with the inclination of the well. The inclination of most wells is more or less pronounced and may, additionally, vary with depth. Thus the cut or dynamic proportion of each phase is different from its volume proportion, referred to as the "static" proportion or "hold-up". The static proportion of one phase is the proportion which is occupied by said phase of a given volume of well as delimited by two transverse cross-sections.

In a two-phase mixture, e.g. of the water-oil type, it is known that the dynamic proportion can be obtained from three parameters, namely: the total flowrate (the instantaneous flowrate of all phases taken together); the static proportion; and a third parameter which is usually the relative slippage velocity of water relative to oil.

Conventionally, the total flowrate is obtained by means of a logging apparatus provided with a flowmeter which may either be of the propeller type (U.S. Pat. No. 3,630,078) or else of the vortex emission type (U.S. Pat. No. 4,442,711). Further, the slippage velocity is usually determined by calculation from values for the static proportion and the relative density, as described for example in U.S. Pat. No. 3,909,603.

The aim of the present invention is to determine the static proportion of one of the phases, and in particular in a flow comprising a mixture of oil and water.

Numerous methods are known for determining the static proportion of each phase. They may be classified into three groups, depending on whether a measurement is performed overall on the entire section of the casing; by sampling a fraction of the flow; or by performing a so-called "local" measurement taken at a point in the flow.

An example of overall measurement is given by measuring the average density of each phase using a differential pressure device or gradient manometer as shown by U.S. Pat. No. 3,455,157. This known device is simple to use, but its accuracy falls off considerably when the flowrate is relatively high i.e. more than about 2000 bbl/d (13 m$^3$/h) and with increasing well inclination.

One known way of performing measurements by sampling, makes use, for example, of two plates of a capacitor placed in the flow with variations in capacitance being measured; another method consists in irradiating a deflected portion of the flow with photons. These types of measurements rely on a sample of the flow and it is never certain that the sample is truly representative of the flow.

Local measurements are spot measurements of a physical characteristic of the phase present at the end of a sensor. The characteristic takes only one given value for each phase because of the small size of the sensor relative to the bubbles of one of the phases flowing in the other phase which is referred to as the "continuous" phase. Since the sensor is disposed at a single point in the flow, a measurement of the static proportion at said point is obtained by integrating measurements over a period of time.

The main known methods of performing local measurements are of the electrical type where resistivity is measured (see, for example, U.S. Pat. No. 3,792,347) or of the optical type where a light ray is refracted at the end of an optical fiber (see the article published in "La Houille Blanche" number 5/1978, pages 351–355), or of the radiofrequency type in which the dielectric constant is measured (see German Pat. No. 2,558,588).

Theoretically, the average value of the static proportion of each phase on the borehole cross-section can be obtained from local measurements by performing measurements at multiple measuring points, an by integrating the local measured values over the entire cross-section of the well. To this end, either a plurality of sensors are used to enable the measurements to be performed simultaneously, with the consequent risk of the flow being disturbed and with various construction difficulties, or else a sensor (or a few sensors) is displaced to each measurement point, thereby giving rise to an unfortunate loss of time.

The present invention makes it possible at each depth to obtain the value of the average static proportion of each phase over the entire well cross-section corresponding to a given depth, with said values being accurate and obtained with considerable saving of time.

SUMMARY OF THE INVENTION

The method in accordance with the invention is based on a discovery made by the present Applicant, whereby there exist, in a two-phase water-oil flow, certain defined points for which the local static proportion is related to the average static proportion by a determined relationship.

To this end, and in accordance with the invention, a method of analyzing a multiphase fluid flowing along a hydrocarbon well in order to determine the average static proportion of at least one of the phases at a plurality of measurement depths of the well by means of local measurements, comprises the steps of: measuring the local static proportion of said one phase at at least one point located on a circle in a transverse cross-section of the well at each of said measurement depths, said circle having a radius r substantially equal to 0.7 R, where R is the radius of the well; and determining the average static proportion of said phase at said depth as a predetermined relationship of the local static proportion at said point.

In a first implementation the method comprises: performing at least one measurement at one of two points Po or Po' having polar co-ordinates r and θ, in the transverse cross-section corresponding to the depth under consideration, such that r is substantially equal to 0.7 R and θ is substantially equal to +80° or −80° measured from the projection of the vertical onto the transverse cross-section; and determining the average static proportion as a value substantially equal to the local static proportion at either of these two points Po and Po'.

Preferably, a measurement is taken at each of the points Po and Po' mentioned above, and the average of these two measurements is taken as the value of the average static proportion. These measurements may be performed either simultaneously by using two sensors or else by using a single sensor which is displaced from one point to the other.

In a second implementation, which is unaffected by the angular position of the tool in the well, the method comprises: measuring the local static proportion of said one phase at a series of points situated on a circle of radius r substantially equal to 0.7 R; determining the variations of the local static porportion as a function of the various angular positions θ of the measurement points; and determining the average static proportion at said depth as the value of said function which has the co-ordinates θ = + or −80° corresponding to one of the defined points Po or P'. This series of measurements may be performed either simultaneously by using a plurality of sensors regularly spaced apart around the circle of radius r=0.7 R, or else by using a single sensor rotating about the central longitudinal axis of the well along said circle.

In a preferred embodiment of the method, the local measurements are performed using a sensor of the radiofrequency type comprising a coaxial cable connected to a high frequency wave generator, and variations in the dielectric constant of the phase in contact with the end of the sensor are measured.

The invention also relates to a well logging apparatus adapted to be suspended in a hydrocarbon well at the end of a cable for analyzing a multi-phase fluid flowing along said well in order to determine the average static proportion of at least one of the phases at a plurality of measurement depths, comprising: a body adapted to be attached to the cable; at least one sensor movably mounted on said body for performing a local measurement sensitive to the phases of the fluid; and means for positioning the sensor at a point substantially located on a circle of radius r which is equal to 0.7 R in the transverse cross-section of the well at each of said measurement depths, where R is the radius of the well.

The apparatus may include one, two, or more arms, each carrying one sensor.

Further, the apparatus body is either excentered on the lower portion of the well wall (when the well is inclined) or else it is centered in the well by centering means.

In a preferred embodiment, the measuring sensor is of the radiofrequency type and is constituted by a coaxial cable connected to a high frequency wave generator and serves to measure the dielectric constant of the phase in contact with the end of the sensor.

BRIEF DESCRIPTION OF THE DRAWINGS

The invention will be better understood from the following description given with reference to the accompanying drawings, in which.

DETAILED DESCRIPTION OF THE INVENTION

The following description relates to determining the static proportion of one of the phases, namely water, in a two-phase water-oil flow. Naturally, the present invention is not limited to this example and is applicable to determining the static proportion of each of the phases in a two-phase water-oil flow or in a three-phase water-oil-gas flow.

In order to better understand the invention and the meaning of the parameter sought, the relationship between the parameters of a two-phase flow comprising water and oil coming from geological formations and flowing along a hydrocarbon well are explained below with reference to FIG. 1.

Figures 1, 2:
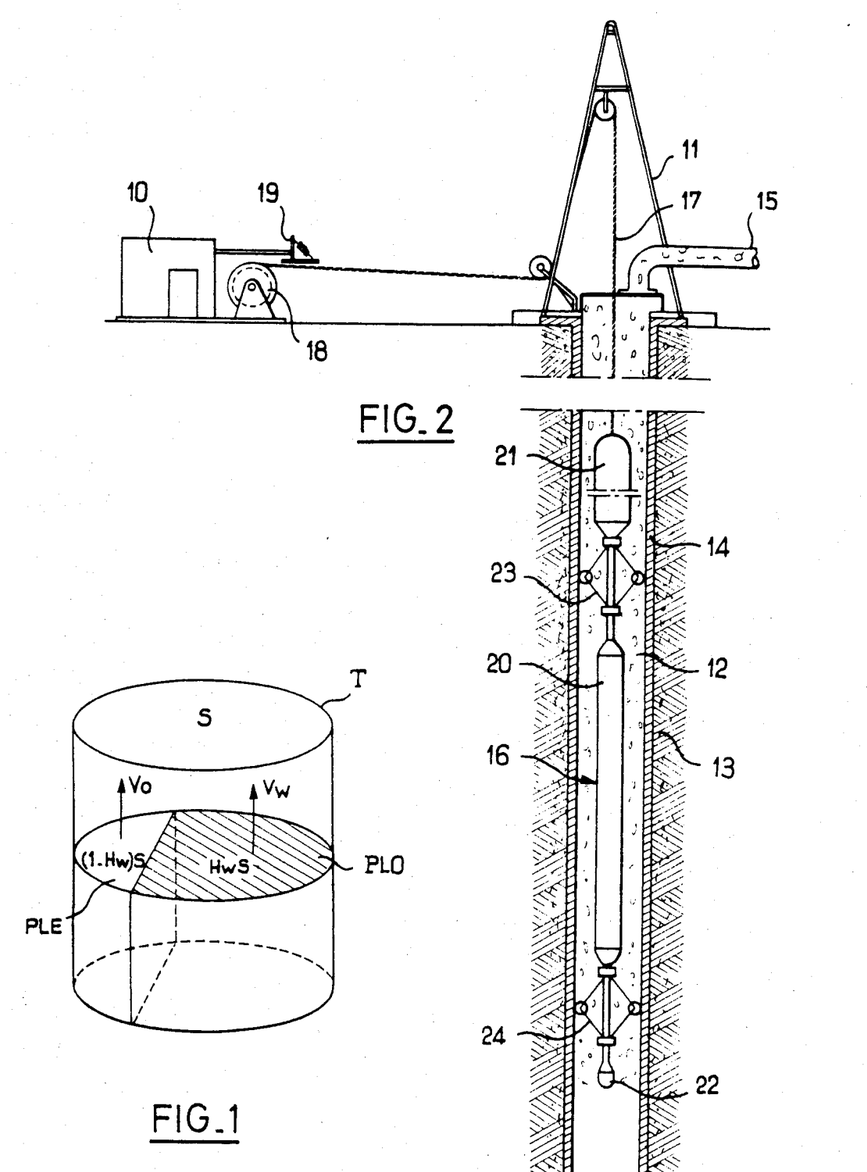
FIG. 1 is a simplified diagram of a two-phase flow in an oil well in production.
FIG. 2 is a diagram showing a logging tool in accordance with the invention in an oil well together with the associated surface equipment.

In FIG. 1, a section of casing T lining the wall of an oil well and having a transverse cross-section of area S is represented by a cylinder. A fluid comprising a light phase PLE (for example oil) and a heavy phase PLO (shaded), for example water, is flowing along the well. For reasons of clarity the two phases are shown as being separate from each other. In reality the two phases are mixed, with one of the phases being in the form of drops in the other phase which is said to be continuous. In the following, Hw (or Ho) designates the static proportion, i.e. the "hold-up" of water (or of oil), i.e. the ratio between the volume of water (or of oil) to the total volume. The oil flowrate Qo, the water flowrate Qw, and the total flowrate Qt are then given by the following equations (where Hw and Ho are average values for the cross-section S):

$$Qo = (1 - Hw) \cdot S \cdot Vo$$

$$Qw = Hw \cdot S \cdot Vw$$

$$Qt = Qo + Qw$$

where Vw and Vo are the respective flow velocities of the water and the oil phases.

The aim of the method and of the apparatus in accordance with the invention is to determine, at various depths, the average value of the static proportion of one of the phases (Hw or Ho) over the entire transverse cross-section of the casing corresponding to the depth at which the measurement is being performed.

FIG. 2 is a diagram showing a surface unit 10 housing means for exploiting data and located close to a drilling rig 11 which is itself disposed above a borehole 12 passing through geological formations 13 which are producing hydrocarbons. The borehole 12 comprises cylindrical casing 14 along which a multi-phase fluid comprising a mixture of water, gas, and oil is flowing. On arrival at the surface, the fluid is removed via a duct 15 towards a storage installation (not shown).

In order to analyze the fluid flowing along the casing 14, use is made of a logging tool 16 suspended at the end of a cable 17 wound on a winch 18. Since measurements are performed at various depths, it is necessary to establish the depths at which measurements are taking place. To this end, the winch 17 has a conventional cable displacement detector 19, for example comprising a pressure wheel engaging the cable 17.

The logging tool comprises an elongate body 20, an upper electronics section 21, a lower nose 22, and means for measuring and processing data which are described in detail below. In the embodiment shown in FIG. 2, the tool 17 is disposed in the middle of the casing 14 by conventional upper and lower centering means 23 and 24.

Reference is now made to FIGS. 3 to 6 and 9 which describe three embodiments of the apparatus in accordance with the invention.

Figures 3, 5:
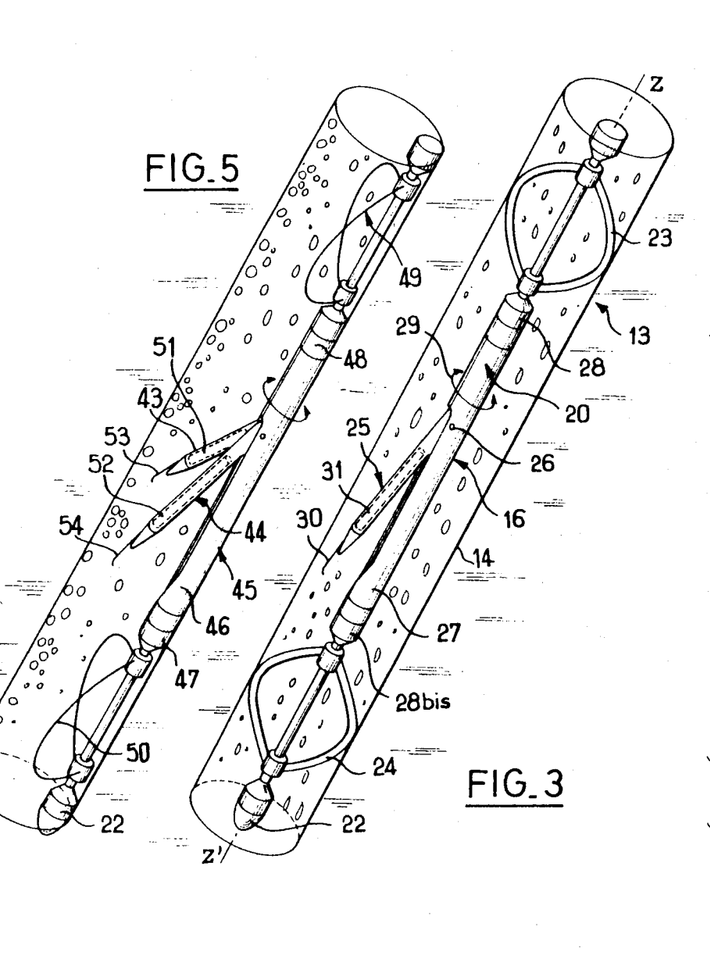
FIGS. 3 and 5 show two embodiments of a tool in accordance with the invention in an inclined well.

In FIG. 3, the logging tool 16 in accordance with the invention comprises the items already described with reference to FIG. 2, which items bear the same references. It is shown centered in a portion of casing 14 lining an inclined well. An arm 25 is mounted on the body 20 and is hinged about a pivot 26 which is orthogonal to the longitudinal axis z—z' of the tool. Conventional actuator means (e.g. the hydraulic type, and not shown) cause the arm 25 to pivot in a diametrical plane of the tool between a retracted position against the body of the tool to enable the tool to be displaced between two measurements, and an extended position at a distance from the body 20 (as shown in FIG. 3) enabling a measurement to be performed.

The body 20 comprises a rotary central section 27 (on which the arm 25 is mounted) located between upper and lower fixed portions 28 and 28bis. The rotary section 27 is rotated in the direction of an arrow 29 by means of a motor and rotary seals (not shown and of conventional type).

The tool includes a measuring sensor whose end 30 is visible in FIG. 3 mounted at the end of the arm 25 and suitable for performing a local (or spot) measurement of a physical characteristic of the phase in contact with the end of the sensor which is immersed in the flow.

An electronic circuit 31 is disposed inside the arm 25 for processing the measured data, and this circuit is described below in detail with reference to FIGS. 11, 12 and 14.

Figure 4:
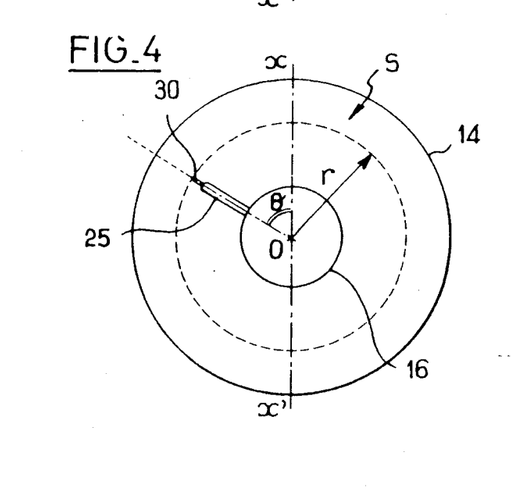
FIGS. 4 and 6 are sections showing the positions in the well of the tools shown in FIGS. 3 and 5 respectively.

FIG. 4 is a diagrammatic section on a transverse cross-section S of the casing 14, showing the tool 16 centered and the arm 25 in the extended or measuring position.

In accordance with the invention, at least one local measurement is performed, at each depth, at a defined point in the flow for which a determined relationship exists between local Hw (as measured) and average Hw (the desired value).

The Applicant has discovered that there exist two defined points Po and Po' in a two-phase water-oil flow for which local Hw is substantially equal to average Hw. The polar $(r, \theta)$ co-ordinates of these points in the plane of the transverse cross-section S, have r substantially equal to 0.7 R where R is the inside radius of the casing, and have $\theta$ substantially equal to $+80°$ and to $-80°$ with reference to the upwardly directed projection of the vertical on the section S. Given the symmetrical flow positions as observed about the vertical, Po and Po' are symmetrically disposed about the projection of the vertical on the transverse cross-section under consideration.

This property holds good for any casing (or well) inclination in the range 0° to 45°C. regardless of the total flowrate from 400 to 6000 bbl/d (2 m³/h to 40 m³/h) and regardless of the dynamic proportion, or cut, of the water (from 10% to 95%).

Figure 7:
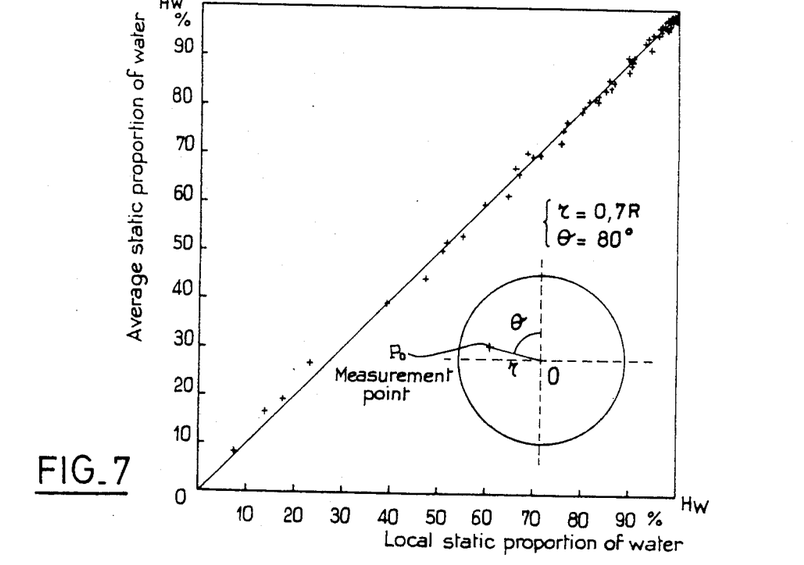
FIG. 7 is a graph showing the variation of the average static proportion as a function of the local static proportion of a plurality of measurements performed at a defined point Po for different dynamic parameters in the flow.
Figure 8:
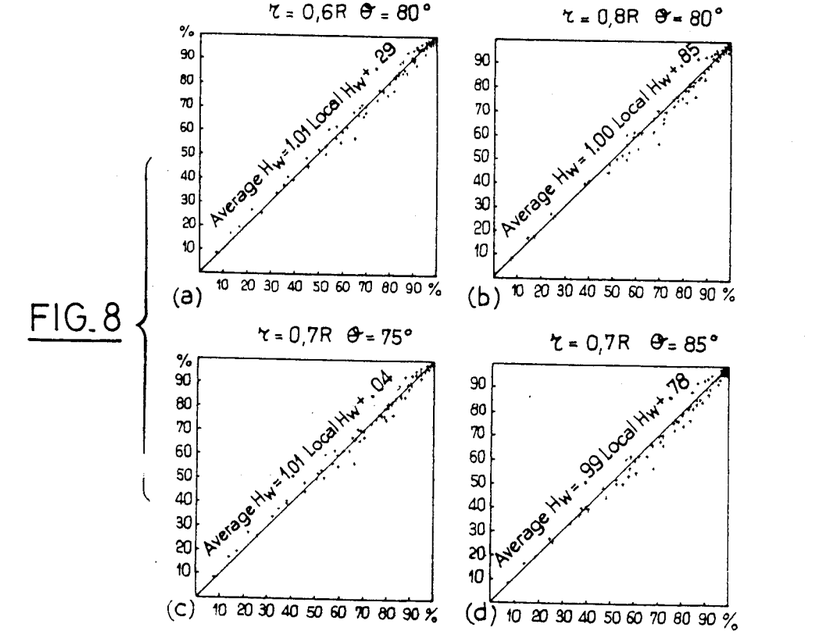
FIGS. 8a, 8b, 8c, 8d are similar to FIG. 7 except that for each curve the measurements were performed at a point close to the defined point Po.

FIG. 7 shows the variation of average Hw as a function of a local Hw, with measurements being performed at the point Po, $r = 0.7$ R and $\theta = +80°$, at various inclinations (from 0° to 45°), for various total flowrates from 400 to 6000 bbl/d (2 m³/h to 40 m³/h), and for various water cuts (10% to 95%).

Further, the Applicant has discovered that the coordinates of the two defined points Po and Po' are not critical. Small errors about these defined points do not significantly modify the linear relationship between local Hw and average Hw, as can be seen in figures 8a to 8d. Each figure shows a series of measurements performed at respective measurement points situated in the vicinity of the defined point Po($r = 0.7$ R and $\theta = 80°$).

The sensor may be placed on the circle of radius $r = 0.7$ R i several different ways.

The radial projection of a pivoting arm such as that shown in FIG. 3 may be controlled by an actuator mechanism associated with a device for measuring the diameter of the well (i.e. of the casing).

Figure 9:
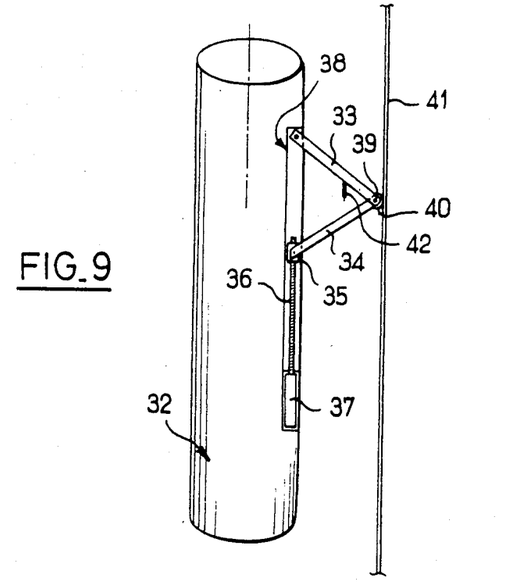
FIG. 9 is a diagram of a variant embodiment of the sensor-carrying arm mechanism.

Or, as shown in the highly diagrammatic view of a FIG. 9, a tool 32 may comprise an arm mechanism including a first arm 33 which is hinged at one of its ends to the tool 32 and at its other end to a second arm 34 which is itself hinged on a nut 35 which is associated with an endless screw 36 fitted to the tool. The screw is rotated by a motor 37 placed together with the screw 36 in a recess 38 in the tool. Displacement of the nut 35 along the screw 36 causes a V-shaped deployment of the two arms 33 and 34 until their common hinge 39 bears the wall of the casing 41 by means of a rolling or sliding 40. A measuring sensor 42 is disposed on the first arm 33 at such a point that the end of said sensor is disposed, when the arm is fully deployed, on the circle of radius 0.7 R. The position of the sensor is thus automatically adjusted as a function of the radius of the casing. Clearly the tool includes as many sets of arms (33, 34) as it includes sensors.

The method in accordance with the invention is described below with reference to two implementations. In a first implementation a measurement is taken at one of the two defined points Po or Po' and the average value of Hw (or Ho) is directly obtained since it is substantially equal to local Hw (or Ho); see FIG. 7. In a second implementation, a plurality of measurements are performed around a circle of radius r substantially equal to 0.7 R and the value of local Hw is deduced from one of the points Po or Po'.

In the first implementation mentioned above, which preferably corresponds to the embodiment shown in FIGS. 3 and 4, a measurement is taken at one of the points Po or Po'. To this end, with the tool centered in the well, the arm 25 is extended until the end 30 of the measuring sensor reaches the circle of radius r=0.7 R. The tool includes measuring means, for example of the gravity type including a pendulum, for giving the angular position of the arm in the well relative to the projection of the vertical on the transverse cross-section. This orientation value is injected into a servocontrol system for the motor which rotates the central portion 27 of the body 20 on which the arm is mounted. The end of the sensor is thus placed in one of the two defined points Po or Po' where r=0.7 R and $\theta = \pm 80°$.

This first implementation is advantageous since only one local measurement is performed and the average value of the static proportion of the phase under consideration (water in the present case) is obtained directly.

In the second of the above-mentioned implementations, which can also be performed using the embodiment shown in FIGS. 3 and 4, a series of measurements are performed at points distributed around a circle of radius r substantially equal to 0.7 R. This second implementation makes it possible to omit the means for measuring the angular position of the tool relative to the vertical.

Figure 10:
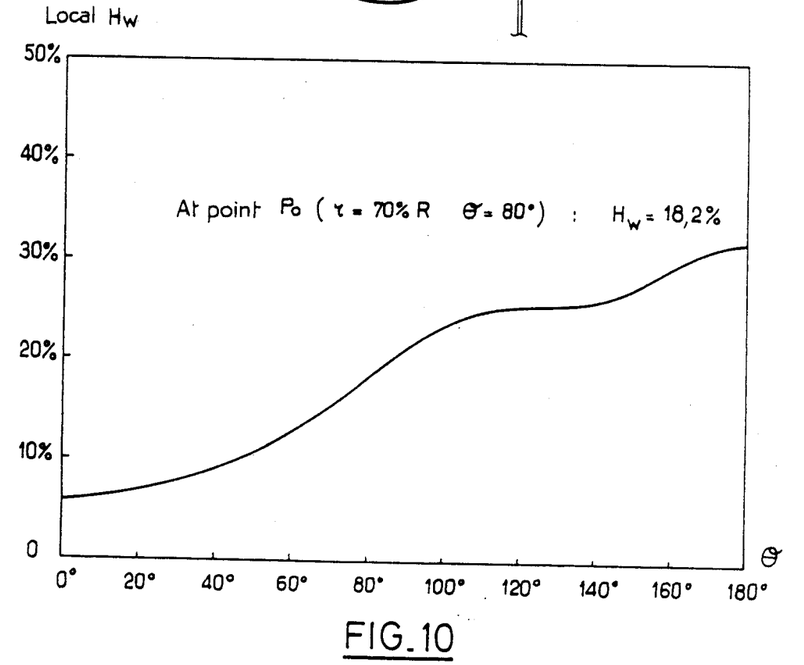
FIG. 10 is a curve giving the value of local Hw as a function of the angular position θ of each measuring point around a semicircle r=0.7 R.

To this end, with the arm 25 in its deployed position so that the end 30 of the sensor lies on a circle of radius r substantially equal to 0.7 R, a first measurement is performed, and then the rotary portion 27 of the body 20 is rotated to bring the arm to some other angular position (i.e. a position having a different value of $\theta$) and measurement is performed. The cycle is continued until a series of measurements is obtained taken at regular intervals around a semicircle r=0.7 R. This series of measured values for Hw is plotted on a (Hw, $\theta$) plane. Then, by linear or polynomial interpolation, a curve is traced giving the variations of local Hw as a function of $\theta$. FIG. 10 shows a particular example of one such curve whose exact shape depends on the dynamic flow conditions. The value of local Hw at $\theta = +80°$ corresponding to the defined point Po is then read on this curve.

Measurements need only be performed at points situated on the left or right semicircle of r=0.7 R, since there are two symmetrical defined points Po and Po', and one of them will always appear on the resulting semicircle.

The above-mentioned plurality of measurements could also be performed simultaneously by means of a tool having a plurality of arms, e.g. three arms, each provided with a measuring sensor. Each arm is at 120° from its neighbors and the sensors are disposed around the same transverse cross-section of the flow. At a given depth, the arms are deployed until the end of each sensor lies on a circle of radius r=0.7 R at arbitrary angular orientation, capable of being determined by the angle-measuring means. All three measurements are performed together and, as a result, three points may be plotted in the (local Hw, $\theta$) plane. In order to restrict $\theta$ to values between 0° and 180°, the value of Hw measured by the third sensor (corresponding to an angle of $\theta$ greater than 180°) is associated with a value of $\theta$ which is symmetrically disposed about the vertical. The curve (such as the one shown in FIG. 10) relating local Hw to the angular orientation $\theta$ of the measurement points is then traced by interpolation, and preferably polynomial interpolation. The value of local Hw for $\theta = +80°$, i.e. corresponding to the point Ho, is then deduced from this curve.

Performing a plurality of measurements and deducing therefrom the local value of the static proportion of the phase under consideration at the defined point Po is very advantageous over the prior art. In the prior art an estimate is obtained by averaging or integrating a high number of measurements over the entire transverse cross-section. In accordance with the invention, an exact value is obtained for the average value of the parameter sought while using only a small number of measurements.

Advantageously, the number of measurements performed is three. This provides good measuring accuracy while limiting the influence of the arms on the flow. Further, the structure of the apparatus is simplified.

Figure 6:
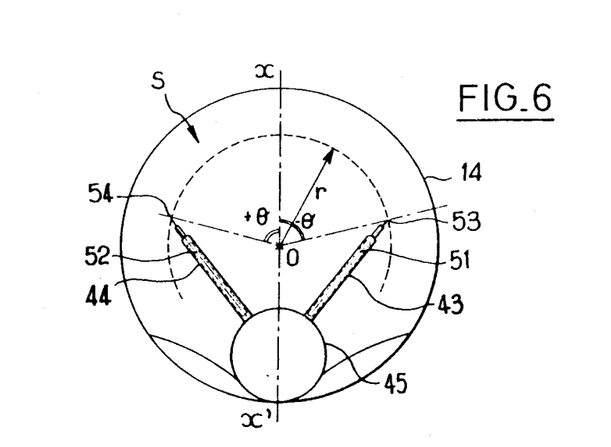

Another embodiment of the apparatus is now described with reference to FIGS. 5 and 6. This embodiment corresponds to a variant of the first embodiment described above. The tool includes two arms 43 and 44 similar to the arm 25 shown in FIG. 3. Both arms are hinged about respective diametrical planes to a rotary section 46 of a body 45, and the body 45 is similarly disposed between upper and lower fixed portions 47 and 48. Upper and lower orienting means 49 and 50 are disposed at each end of the body 45 in order to hold the tool body against the lower portion of the well (or casing) with the arms 43 and 44 oriented towards the upper portion of the well. FIG. 6 is a transverse cross-section of area S corresponding to a given depth and shows the position of the tool. Each orienting means 49, 50 is conventional and comprises two bows disposed in a U configuration and pressed against the wall of the well. When the tool comprises two or more arms, the electronic circuit is preferably located in the body of the tool in order to reduce the diametrical area of each arm and thus to reduce the influence of the arms on the flow.

Respective electronic circuits 51 and 52 similar to the circuit 31 of the arm 25 (see FIG. 3) are disposed in each of the arms 43 and 44. The arms 43 and 44 are disposed on and hinged to the body 45 in such a manner that when the tool rests on the lower portion of the well wall, the end of each sensor 53 and 54 associated with each arm is placed at one of the points Po and Po', whose polar co-ordinates are substantially equal to r=0.7R, and $\theta = +80°$ or $J = -80°$ as the case may be. The resulting local measurements are then averaged.

This embodiment is particularly advantageous since it enables two measurements to be performed simultaneously, thereby avoiding inaccuracies which may occur in arm positioning, since the values of local Hw are theoretically equal at both points.

In the above described tool, any suitable local measurement sensor may be used regardless of its type. However, in a preferred embodiment of the invention, the logging tool incorporates a radiofrequency type local sensor as described hereinafter.

A radiofrequency type measuring apparatus comprises a high frequency electromagnetic wave generator connected at one end to a sensor constituted by a coaxial cable whose other end is placed in the flow. This other end is sufficiently small compared with the size of the drops present in the continuous phase to be in contact either with the continuous phase or else with a drop constituted by the other. The electromagnetic wave is reflected differently depending on the nature of the phase in contact with the end of the sensor and the amplitude and the phase of the reflected wave depend on the impedance of the fluid in contact with the end of the sensor. The use of high frequencies serves to reduce (or to eliminate) the influence of the resistive component and the inductive component. The variations in impedance can thus be considered as being variations in capacitance. Variations in the dielectric constant of the phase in contact with the end of the sensor are thus measured.

The purpose of the associated electronic circuit is to process the amplitude of the phase variation. When two fluid phases are mixed, the phase of the electromagnetic wave varies between two levels, depending on whether the end of the sensor is in oil or in water. The measured magnitude, constituting the output signal, is a voltage which is directly related to phase variation and, consequently, to the dielectric constant of the fluid phase in contact with the end of the sensor.

Figure 11:
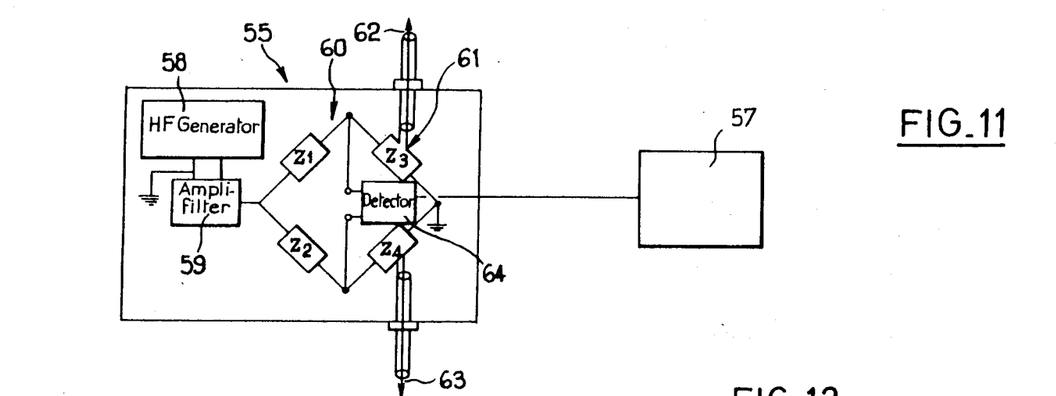
FIG. 11 is a schematic diagram of the electronic circuit associated with the sensor.

FIG. 11 is a block diagram of such an electronic circuit. The circuit comprises a high frequency (HF) portion 55 and a low frequency portion 57 for digitally processing the signal. In the embodiments of FIGS. 3 to 6, only the HF portion 55 of the circuit is disposed in the arm. The HF portion comprises a generator 58 for generating electromagnetic waves at a constant frequency in the GHz range, e.g. at 1 or 2 GHz. The output from the generator 58 is connected to an amplifier associated with a low pass filter (in the present case an amplifying filter block 59). The output from the amplifying filter block 59 is connected to the end of one branch of a Wheatstone bridge. The sensor 61 constituted by a coaxial cable has a first measuring portion 62 whose end is placed in the flow and a second, reference portion 63 which is disposed in air inside the arm. The measuring 62 of the sensor (impedance Z3) is placed in one branch of the bridge 60 while the reference portion 63 (impedance Z4) of the sensor is placed in another branch, and the other branches are connected to the generator 58 via the amplifying filter block 59. A detector placed at the center of the bridge delivers a measurement signal representative of bridge unbalance. The measurement principle is to detect and analyze bridge unbalance, which is characteristic of the nature of the fluid phase in contact with the end of the measuring portion 62 of the sensor 61.

Figure 12:
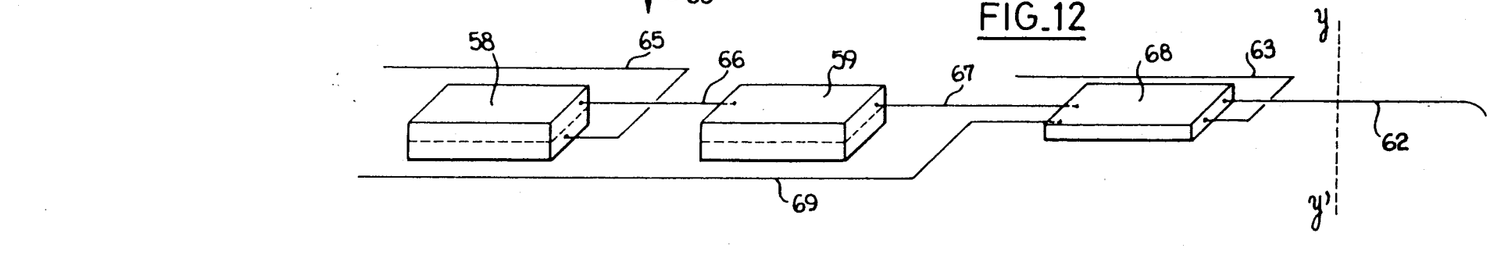
FIG. 12 is a perspective diagram of the high frequency portion of the electronic circuit disposed in an arm.

FIG. 12 is a perspective diagram of the HF portion 55 of the electronic circuit as disposed in one arm of the tool. The items which are common to FIG. 11 have the same references. The generator 58 is fed by a line 65 and its output is connected via a line 66 to the amplifying filter block 59. The output from the block 59 is connected via a line 67 to a block 68 which includes the bridge 60 and the detector 64. The reference and measurement portions 63 and 62 of the sensor 61 are connected to said block 68. A line 69 transmits the measurement signal to the low frequency analog portion 56 of the circuit (located outside the arm).

The reference portion 63 of the sensor is folded back in order to take up less room and it is at the same temperature as the measurement portion 62, and at atmospheric pressure. The measurement 62 of the sensor is by definition at the same pressure and temperature as exists inside the well. In FIG. 12 dotted line segment y—y' symbolizes the boundary in the longitudinal direction between the inside and the outside of the arm.

Figure 13:
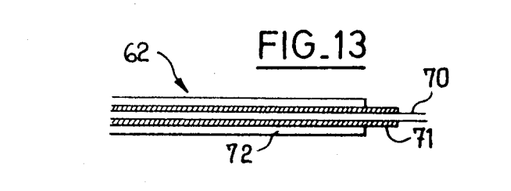
FIG. 13 is a diagram of the end of a measuring sensor.

The end of the measurement portion 62 of the cylindrical measuring sensor is shown diagrammatically in longitudinal section in FIG. 13. The central conductor 70 projects (by about 1 mm) from the insulating sheath 71 which itself extends (by about 5 mm) beyond the outer conductor 72 whose diameter is about 3 mm. These values are given purely by way of example.

The Wheatstone bridge circuit cancels the influence of the temperature conditions which may be arduous down hole. The total length of the cable constituting the sensor 61 is adjustable, and is initially adjusted so as to ensure that the bridge 60 is in balance when both portions 62 and 63 of the sensor are placed in air.

In operation, the output signal from the bridge is equal to the difference between the two signals reflected from the ends of the measurement portion 62 and the reference portion 63 of the cable. The response of the measuring sensor is phase shifted relative to the reference response (located in air), the phase shift ($\Delta\phi$) being:

$$\Delta\phi = 2 \text{ Arctan } (\Delta C \cdot \omega / Z)$$

where $\Delta C$ is the capacitance variation, $\omega$ the inverse of the frequency, and Z the impedance.

Accordingly, the phase shift is greater when the measuring portion of the sensor is in water than when it is in oil. The variations in capacitance at the end of the measuring portion 62 of the sensor cause phase variations in the reflected wave. For example the variation may be about 1.5 pF, with a cable having an impedance of 50 ohms. It can be seen from the above values that the change in phase increases with increasing frequency, whence the advantage of using high frequencies. whence the advantage of using high frequencies.

Figure 14A:
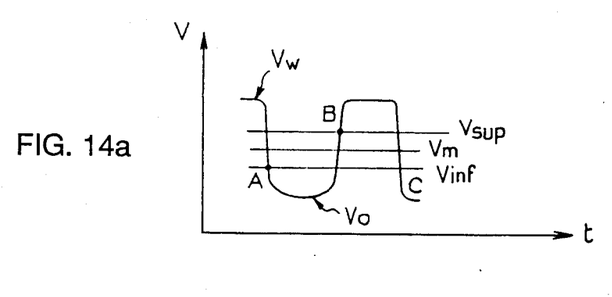
FIGS. 14(a) and 14(b) are waveform diagrams showing signals at various stages of being processed by the electronic circuit.
Figure 14B:
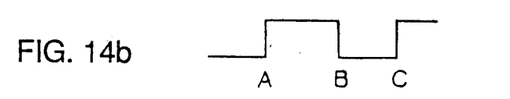

FIGS. 14(a) and 14(b) show an embodiment of the digital processing performed in the portion 57 of the circuit. Curve 14(a) is an example of the signal waveform at the output from the detector 64. The processing produces a digital signal having a value equal to 1 when the phase is oil and to 0 when the detected phase is water as shown on FIG. 14(b). The processing comprises the following steps.

The signal from the detector is sampled at a frequency which can be 1 MHz for example. The sampled values are compared to lower and upper thresholds Vinf and Vsup which are defined as a function of the minimum and maximum signal values Vo and Vw in order to be modified as a function of the dynamic range of the signal. As shown in FIG. 14(a), the thresholds Vinf and Vsup are equally spaced from the middle value Vm=0.5 (Vw −Vo) and such that their difference (Vsup−Vinf) is equal to a predetermined ratio of the difference (Vw−Vo) between the extreme values of the signal. The extreme values Vinf and Vsup of the signal are determined by sampling the signal at a frequency of 1 KHz, for example, and by updating the results of the preceding sampling if necessary: when a new sample is not included in the range defined by the preceding extreme values, this new sample is taken as a replacement value of the minimum or maximum value, as the case may be. This process is continued during a time interval which may be about ten seconds, after which the extreme values are set to predetermined initial values.

The crossings of the thresholds by the measurement signal are detected as indicated hereinafter. A first crossing indicated by reference A, is defined along a decreasing portion of the signal when the signal crosses the lower threshold Vinf. This is equivalent to detecting a crossing of lower threshold Vinf immediately following a crossing of upper threshold Vsup. A second crossing indicated by reference B, is located on the following increasing portion and is defined as the first crossing of the upper threshold Vsup which follows point A. The next point C is determined as indicated for point A.

The occurrence times of points A, B, C,... define a digital signal 14(b) having a value of 1 when the detected phase is oil and the 0 value when the detected phase is water. The static proportion of the oil phase is computed as the proportion of the total time during which the digital signal of FIG. 14(b) takes the 1 value, the total time interval possibly being selected as several tens of seconds.

The method in accordance with the invention may also be used to determine, with a fair degree of accuracy, the locations where water or oil enter the well.

The Applicant has also discovered that for high static proportions of water (greater than 90%) and for a given position of the measuring point, the relationship between average Hw and local Hw remains linear.

Figure 15:
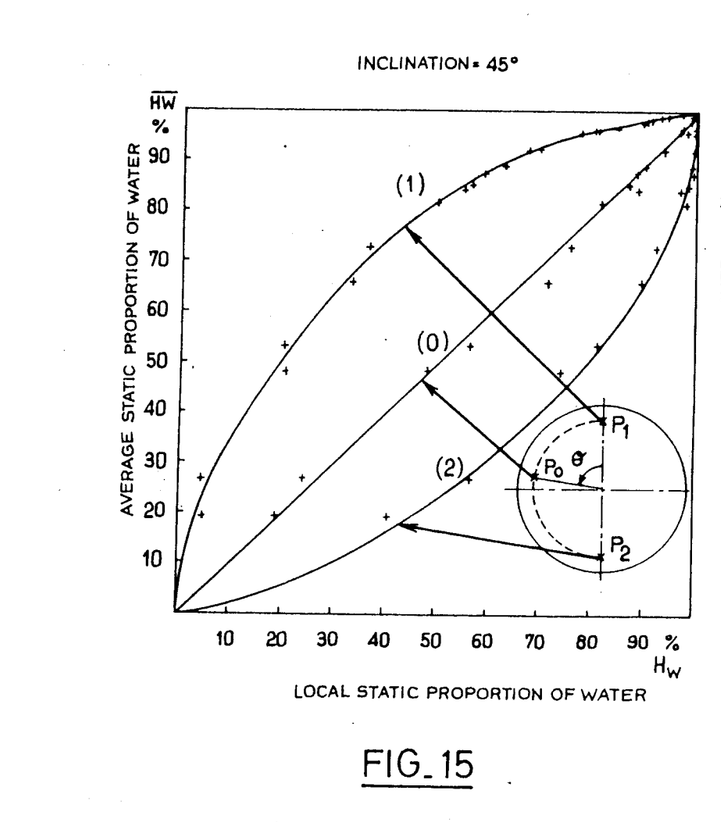
FIG. 15 shows three curves similar to the FIG. 7 curve and respectively corresponding to three measurement points Po, P1 and P2 for a well inclination of 45° and for various dynamic flow conditions.

FIG. 15 shows sets of points forming curves (0), (1), and (2) representative of variations in average Hw as a function of local Hw. Local Hw is measured at three measuring points P0, P1, and P2 for a fixed well inclination of 45° and at different total flowrates and at different dynamic proportions of water.

Figure 16:
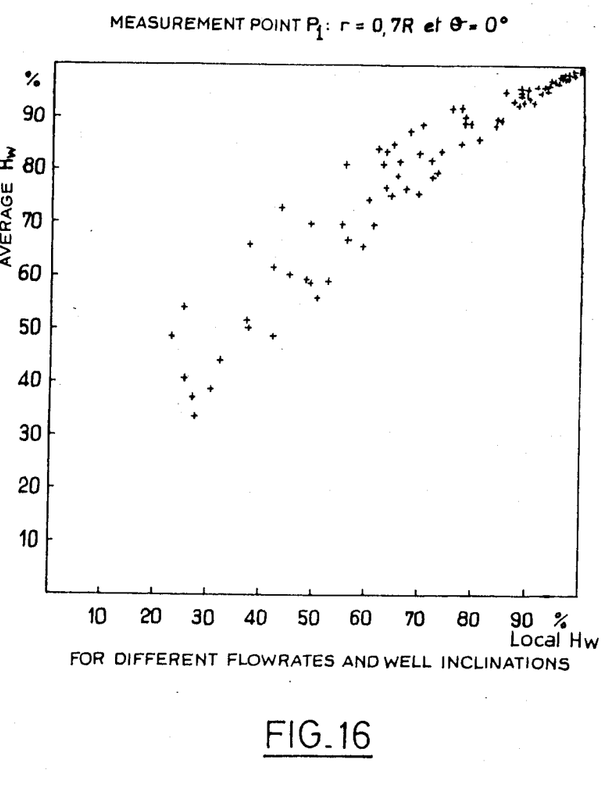
FIG. 16 shows values of average Hw as a function of local Hw measured at the point P3 for various flowrates and well inclinations, and for relatively low static proportions of water.

FIG. 16 shows a variation of average Hw as a function of local Hw measured at the point P1 (r=0.7 R and $\theta=0°$) for different inclinations of the well, for different low dynamic proportions of oil and for different flowrates. Those skilled in the art will appreciate that for average static proportions of water greater than 80%, average Ho (equal to 100%-average Hw) is approximately equal to half local Ho (equal to 100%-local Hw). Thus, accuracy can be improved by performing measurements at a point P1 ($\theta=0°$) at which the slope of the line of average Hw as a function of local Hw is less than the corresponding slope at the point P0 (where the slope is unity). A relatively large variation in local Hw thus corresponds to a relatively small variation in average Hw. Similarly, when the average static proportion of water is relatively low (less than 10%) a measurement is taken at point P2 (r=0.7 R and $\theta=180°$). Thus, the static proportion of oil is determined more accurately since the slope of the line is less than 1 (see the lower portion of the curve (2) in FIG. 15).

In practice, the following steps are performed. After determining the value of the static proportion of water by implementing the above-described method, and as a function of said measurement, the position of the measuring point is adjusted. If the value is low (less than 10%) a measurement is performed at point P2 to determine the static proportion of water Hw with greater accuracy. Inversely, if the static proportion of water is high (greater than 90%) a measurement is performed at point P1 to determine the static proportion of oil Ho more accurately. The static proportion of the less common phase in the flow can thus be measured accurately.

There has been described and illustrated herein methods and apparatus for analzying a multi-phae flow in a hydrocarbon well. While particular embodiments have been disclosed, it should be appreciated that there is no intent to be limited thereby, but rather it is intended that the invention be as broad in scope as the art will allow. Therefore, it will be apparent to those skilled in the art that modifications can be to the described invention without deviating from the scope and spirit of the invention as so claimed.

I claim:

1. A method of analyzing a multiphase fluid flowing along a hydrocarbon well in order to determine the average static proportion Po of at least one of the phases at a depth of the well, comprising the steps of:

measuring a local static proportion of said one phase, at at least one point on a circle located in the transverse cross-section of the well at said measurement depth, said circle having a radius r substantially equal to 0.7 R, where R is the radius of the well; and determining the average static proportion of said phase at said depth as a predetermined relationship of the local static proportion at said at least one point.

2. A method according to claim 1, comprising the steps of:

measuring the local static proportion of said one phase in a zone centered on one of the points (Po, Po') having polar co-ordinates (r, $\theta$) in said transverse cross-section such that r is substantially equal to 0.7 R and that $\theta$ is substantially equal to $+80°$ or $-80°$, with the angle $\theta$ being measured from the projection of the vertical on the transverse cross-section; and determining the average static proportion at said depth as a value substantially equal to the local static proportion at said one point.

3. A method according to claim 1, comprising the steps of:

measuring the local static proportion of said one phase in zones centered on each of the points (Po, Po') having polar co-ordinates (r, $\theta$) in said transverse cross-section such that r is substantially equal to 0.7 R and that $\theta$ is substantially equal to $+80°$ or $-80°$, with the angle $\theta$ being measured from the projection of the vertical on the transverse cross-section; and determining the average static proportion at said depth as a value substantially equal to the average of said measured local static proportion at said points Po and Po'.

4. A method according to claim 3, wherein the measurings at said points Po and Po' is performed simultaneously by means of two sensors.

5. A method according to claim 3, wherein the measurings at said points Po and Po' is performed by a single sensor which is displaced from one point to the other.

6. A method according to claim 1, comprising the steps of:
    measuring the local static proportion of said one phase at a series of measurement points situated on a circle of radius r substantially equal to 0.7 R in the transverse cross-section of the well;
    determining the variations in the local static proportion as a function of the various angular positions $\theta$ of the measurement points on said circle; and
    determining the average static proportion at said depth as the value of said function which has the co-ordinates $r = 0.7$ R and $\theta = +$ or $-80°$.

7. A method according to claim 6, wherein said measuring step comprises performing a series of simultaneous measurements by means of a plurality of sensors regularly spaced apart on the circle of radius $r = 0.7$ R.

8. A method according to claim 6, wherein said measuring step comprises performing a series of measurements by displacing a single sensor around a circle of radius $r = 0.7$ R.

9. A method according to claim 1, further comprising the step of adjusting the position of the measuring point on a circle $r = 0.7$ R as a function of a value of the average static proportion of the heaviest phase.

10. A method according to claim 9, wherein said measuring step comprises measuring the local static proportion of the heavier phase at a point P2 having polar co-ordinates r substantially equal to 0.7 R and $\theta$ substantially equal to 180°; and said determining step comprises determining the average static proportion Hw of the heavier phase as substantially equal to one-half the value of the local static proportion at said point P2.

11. A method according to claim 9, wherein said measuring step comprises measuring the local static proportion of the lighter phase at a point P1 having polar co-ordinates r substantially equal to 0.7 R and $\theta$ substantially equal to 0°, and said determining step comprises determining the average static proportion Ho of the lighter phase as substantially equal to one-half the value of the local static proportion at said point P1.

12. A method according to claim 1, wherein said step of measuring the local static proportion of said one phase at a point comprises: emitting a radiofrequency signal into the fluid at said point through a coaxial cable; and measuring the variations of the dielectric constant of the fluid at said point.

13. A well logging apparatus adapted to be suspended to a cable in a hydrocarbon well for analyzing a multiphase fluid flowing along said well in order to determine the average static proportion of at least one of the phases at a plurality of measurement depths, comprising:
    an elongate body;
    at least one sensor movably mounted on said body and sensitive to the phases of the fluid for performing a local measurement in a limited zone of the well; and
    means for positioning said sensor at a point substantially located on a circle of radius r which is equal to 0.7 R in the transverse cross-section of the well at each of said measurement depths, where R is the radius of the well.

14. An apparatus according to claim 13, comprising an arm on which said sensor is fixed, said arm being pivotally mounted on said body about an axis perpendicular to the longitudinal direction of said body.

15. An apparatus according to claim 13, comprising:
    at least two arms pivotally mounted on said body about corresponding axes perpendicular to the longitudinal direction of said body each of said arms carrying one sensor and
    means for simultaneously driving said arms so that said sensors are maintained on said circle of radius r in the transverse cross-section of the well.

16. An apparatus according to claim 13, further comprising means for centering said body in the well, said means being disposed longitudinally above and below a portion of the body on which said at least one sensor is mounted.

17. An apparatus according to claim 13, further comprising means for excentering said body against the lower portion of the wall of the well.

18. An apparatus according to claim 17, wherein said excentering means comprises first and second resilient blade means respectivelly mounted above and below the body portion on which said at least one sensor is mounted, each of said resilient blade means including a U-shaped configuration of arcuate blades.

19. An apparatus according to claim 16, comprising three arms each pivotally mounted on said body about an axis perpendicular to the longitudinal direction of said body, said arms being regularly spaced apart about the longitudinal direction of said body, and each of said arms carrying one sensor.

20. An apparatus according to claim 13, further comprising means for detecting the angular position of the body about the longitudinal direction of the well with respect to a reference position related to the vertical.

21. An apparatus according to claim 20, further comprising means, responsive to said angular position detecting means, for rotating the body about the longitudinal axis of the well, thereby maintaining said at least one sensor at a selected angular position about the longitudinal direction of the well.

22. An apparatus according to claim 13, wherein said at least one sensor is of the radiofrequency type including a coaxial cable for providing a measurement signal which is a function of the dielectric constant of the phase of the fluid in contact with the end thereof.

23. An apparatus according to claim 22, comprising an arm mounted on said body and carrying said sensor, and by further comprising an electronic circuit for processing the measurement signal, said circuit including a high frequency portion located in said arm.

24. A method according to claim 1, further comprising repeating said measuring and determining steps at a plurality of measurement depths of the well in order to determine the average static proportion of said phase at each measurement depth.

* * * * *